United States Patent
Peterson et al.

(10) Patent No.: US 7,272,444 B2
(45) Date of Patent: Sep. 18, 2007

(54) MEDICAL DEVICE INTERFACE SYSTEM WITH AUTOMATIC RATE THRESHOLD ADJUSTMENT

(75) Inventors: Les Norman Peterson, Woodbury, MN (US); Paula Dieterle, Champlin, MN (US); Par Lindh, Maple Grove, MN (US); James Kalgren, Lino Lakes, MN (US); James O. Gilkerson, Stillwater, MN (US); Dorothy Marie Naumann, Stillwater, MN (US); Kenneth H. Persen, Maple Grove, MN (US); Mark Joseph Schwartz, White Bear Lake, MN (US); Tala L Bynum, Rogers, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 366 days.

(21) Appl. No.: 10/841,966

(22) Filed: May 6, 2004

(65) Prior Publication Data

US 2005/0010258 A1 Jan. 13, 2005

Related U.S. Application Data

(60) Provisional application No. 60/468,946, filed on May 7, 2003.

(51) Int. Cl.
*A61N 1/37* (2006.01)
(52) U.S. Cl. .............................. 607/30; 607/31; 607/32; 607/59; 607/60; 607/27
(58) Field of Classification Search .................... 607/4, 607/5, 9, 14, 15, 17, 30–32, 59, 60; 600/523; 128/903
See application file for complete search history.

(56) References Cited

U.S. PATENT DOCUMENTS

| | | | | |
|---|---|---|---|---|
| 5,292,341 A | * | 3/1994 | Snell | 607/30 |
| 5,607,460 A | * | 3/1997 | Kroll et al. | 607/30 |
| 6,289,248 B1 | * | 9/2001 | Conley et al. | 607/59 |
| 6,522,925 B1 | * | 2/2003 | Gilkerson et al. | 607/30 |
| 7,003,349 B1 | * | 2/2006 | Andersson et al. | 600/523 |
| 7,085,604 B2 | * | 8/2006 | Turney et al. | 607/30 |
| 2003/0176899 A1 | * | 9/2003 | Samuelsson et al. | 607/60 |

(Continued)

FOREIGN PATENT DOCUMENTS

WO WO 01/43822 * 6/2001

*Primary Examiner*—Carl Layno
*Assistant Examiner*—Eugene Wu
(74) *Attorney, Agent, or Firm*—Schwegman, Lundberg, Woessner & Kluth, P.A.

(57) ABSTRACT

A medical device programmer automatically adjusts parameters to be programmed to a medical device in response to a user modifying related parameters. Slide controllers on the programmer display screen can adjust parameters. In response to slide controller movement, the programmer automatically adjusts related parameters by moving their slide controllers. This graphically illustrates to the user the automatic adjustments being made to the related parameters. and the relationship between parameters being adjusted by the user and automatically. In response to on screen parameter changes, the system graphically illustrates the parameter values that are changed and those that are programmed to the medical device and those that would cause unsafe condition in the medical device if programmed. The method also prevents the programming to the medical device the parameters that would cause an unsafe condition.

25 Claims, 6 Drawing Sheets

U.S. PATENT DOCUMENTS

2004/0064062 A1* 4/2004 Zhou et al. .................. 600/515
2004/0088020 A1* 5/2004 Condie et al. ................ 607/30
2004/0111131 A1* 6/2004 Hu et al. ...................... 607/60
2005/0033385 A1* 2/2005 Peterson et al. .............. 607/60

* cited by examiner

MEDICAL DEVICE INTERFACE SYSTEM WITH AUTOMATIC RATE THRESHOLD ADJUSTMENT

RELATED APPLICATION

This application claims the benefit of provisional application U.S. Ser. No. 60/468,946 filed on May 7, 2003, entitled "MEDICAL DEVICE INTERFACE SYSTEM AND METHOD", Peterson et al.

FIELD OF INVENTION

The present invention relates to programming devices used to program implantable programmable medical devices, such as cardioverter-defibrillators and pacemakers. More particularly, but not by way of limitation, the present invention relates to improvements in the graphical user interface of the programmer devices, wherein the graphical user interface automatically communicates to the programming device user in real-time suggested changes in parameters in response to the user's modification of related parameters. The programming device graphical user interface improvements also include a method of preventing parameter modification that creates unsafe conditions.

BACKGROUND OF THE INVENTION

Implantable cardiac rhythm CRM devices, more specifically, cardiac defibrillators (ICDs) are well established therapeutic devices for treating patients who have experienced one or more documented episodes of hemodynamically significant ventricular tachycardia or ventricular fibrillation. Since their clinical inception more than two decades ago, ICDs have evolved from basic to sophisticated electronic devices that provide physicians with a variety of clinically useful functions with which to treat patients.

Presently, even the most basic ICDs typically have more than one tachycardia detection criterion, tiered therapy which combines bradycardia support pacing with various antitachycardia pacing modes, low-energy cardioversion, defibrillation, and data logging capabilities. The data logging capabilities within ICDs have become increasingly important, since the amount of data required for the ICDs operation increases proportionally with the increase in ICD functions. Efficiently processing this large amount of data has become possible with the incorporation of microprocessors and memory with the ICD.

Once an ICD has been implanted, the physician interacts with the ICD through a clinical programmer. The clinical programmer is used to establish a telemetric link with the implanted ICD. The telemetric link allows for instructions to be sent to the electronic circuitry of the ICD and clinical data regarding the occurrence and treatment of a patient's cardiac arrhythmias and the ICD's operation to be sent from the electronic circuitry of the ICD to the programmer. The typical programmer is a microprocessor based unit that has a wand for creating the telemetric link between the implanted ICD and the programmer, and a graphics display screen that presents a patient's recorded cardiac data and ICD system information to the physician.

As ICD feature sets become richer and more complex, ICDs are getting increasingly more complicated to program. This is especially the case in situations where modifications of one feature ripples through and interacts with other selected features.

For ICDs it can be very difficult for physicians to deal with non-compatibilities with programming. Such devices may have many features to program and, when physicians go in to program, there may be some inconsistencies that are not recommended by logic or by concerns for safety of the patient. In the past, these inconsistencies were displayed as error messages and the physician often had to wade through a series of screens to determine the nature of the inconsistency and how to resolve it.

In addition, physicians were frustrated by error messages, which note an interaction but did not tell them what to do resolve the problem. They were often reduced to trial and error programming which might create a second parameter interaction while resolving the first.

In addition, for devices currently on the market, device parameters are set by selecting from a list of possible options via the programmer. The options have typically been scattered throughout the programmer user interface.

What is needed is a more intuitive way for the physician to resolve parameter interactions and a user interface that allows related parameters to be displayed simultaneously to enhance physician resolution of such parameter interaction conflicts.

SUMMARY OF THE INVENTION

A medical device system having a medical device and a programming interface, wherein the programming interface provides a method of automatically adjusting parameters to be programmed to a medical device in direct response to a user modifying related parameters that are to be programmed to the medical device. The programming interface is comprised of a graphical user interface including slide controllers that are engaged on the display screen by the system user to graphically modify related parameters on screen. In response to the on screen parameter changes implemented by the user via slide controller movement, the programmer automatically adjusts related parameters on the display screen by moving slide controllers for related parameters. This automatic adjustment by the programmer graphically illustrates to the user the automatic adjustments being made to the related parameters, which thereby prevent the creation of unsafe conditions. The automatic adjustment also graphically illustrates the relationship between parameters being adjusted by the programmer user and the related parameters that are automatically adjusted by the programmer. In response to on screen parameter changes, the system graphically illustrates the parameter values that are changed and those that are programmed to the medical device and those that would cause unsafe condition in the medical device if programmed.

These and various other features, as well as advantages, which characterize the present invention, will be apparent from a reading of the following detailed description and a review of the drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE PREFERRED EMBODIMENT

In the following detailed description, reference is made to the accompanying drawings that form a part hereof, and in which is shown by way of illustration specific embodiments or examples. These embodiments may be combined, other embodiments may be utilized, and structural, logical and electrical changes may be made without departing from the spirit and scope of the present invention. The following detailed description is therefore, not to be taken in a limiting sense, and the scope of the present invention is defined by the appended claims and their equivalents.

The present invention is an improved graphical user interface of a programmer used within a medical device system, wherein the medical device system is comprised of a medical device and a medical device programmer. The medical device programmer provides a method for automatically adjusting rate threshold parameters to be programmed to a medical device in direct response to a user modifying related rate threshold parameters that are to be programmed to the medical device. The programmer graphical user interface utilizes slide controllers that are engaged on the display screen by the system user to modify rate threshold parameters. In response to the on screen rate threshold parameter adjustments implemented by the user via slide controller movement or engaging a pop-up menu that includes a plurality of numbers that are displayed upon engagement of the rate control window within each slide controller. The programmer automatically adjusts related rate threshold parameters on the display screen by automatically moving slide controllers for related threshold parameters. This automatic adjustment by the programmer graphically illustrates to the user the automatic adjustments being made to the related rate threshold parameters by the programmer. The automatic responsive adjustment function that adjusts related rate threshold parameters in response to user parameter adjustments is controlled by programmer rules that dictate levels and ranges for related threshold rates so as to prevent the creation of unsafe conditions caused by conflicts in the parameters. The automatic responsive adjustment function also graphically illustrates the relationship between rate threshold parameters being adjusted by the programmer user and the related rate threshold parameters that are automatically adjusted by the programmer.

Another aspect provided by the improved graphical user interface is the ability of the programmer to provide for the graphical setting, adjusting and visualizing of device timing behavior. The improved graphical user interface provides the programmer user with the ability to graphically communicate how cardiac conditions relate to particular parameters as the user adjusts parameters such as Atrioventricular delay (AV delay), left ventricular offset (LV offset), post-ventricular atrial refractory period (PVARP) right ventricular refractory period (RVRP), and left ventricular refractory period (LVRP). It also allows the programmer user with the ability to graphically resolve potentially unsafe conditions and undesirable states resulting from the adjustment of parameters. It further allows the user to visualize the graphic relationship between timing parameters such as AV delay, LV offset, PVARP, RVRP and LVRP while facilitating the user's ability to graphically adjust the atrial and ventricular timing settings using parameter control sliders. It also uses color codes to illustrate the relationship between different atrial and ventricular timing settings.

The present system and methods are described with respect to implantable cardiac rhythm management (CRM) devices, such as pacemakers, cardioverter defibrillators (ICDs), pacer/defibrillators, and multi-chamber and/or multi-site (in a single chamber or multiple chambers) cardiac resynchronization therapy (CRT) devices that utilize standard pacing and defibrillating leads. Notwithstanding, it is contemplated that the present invention and methods may be used in alternative embodiments with CRM devices that are not using standard pacing and defibrillating leads or with CRM devices that are leadless.

Figure 1:
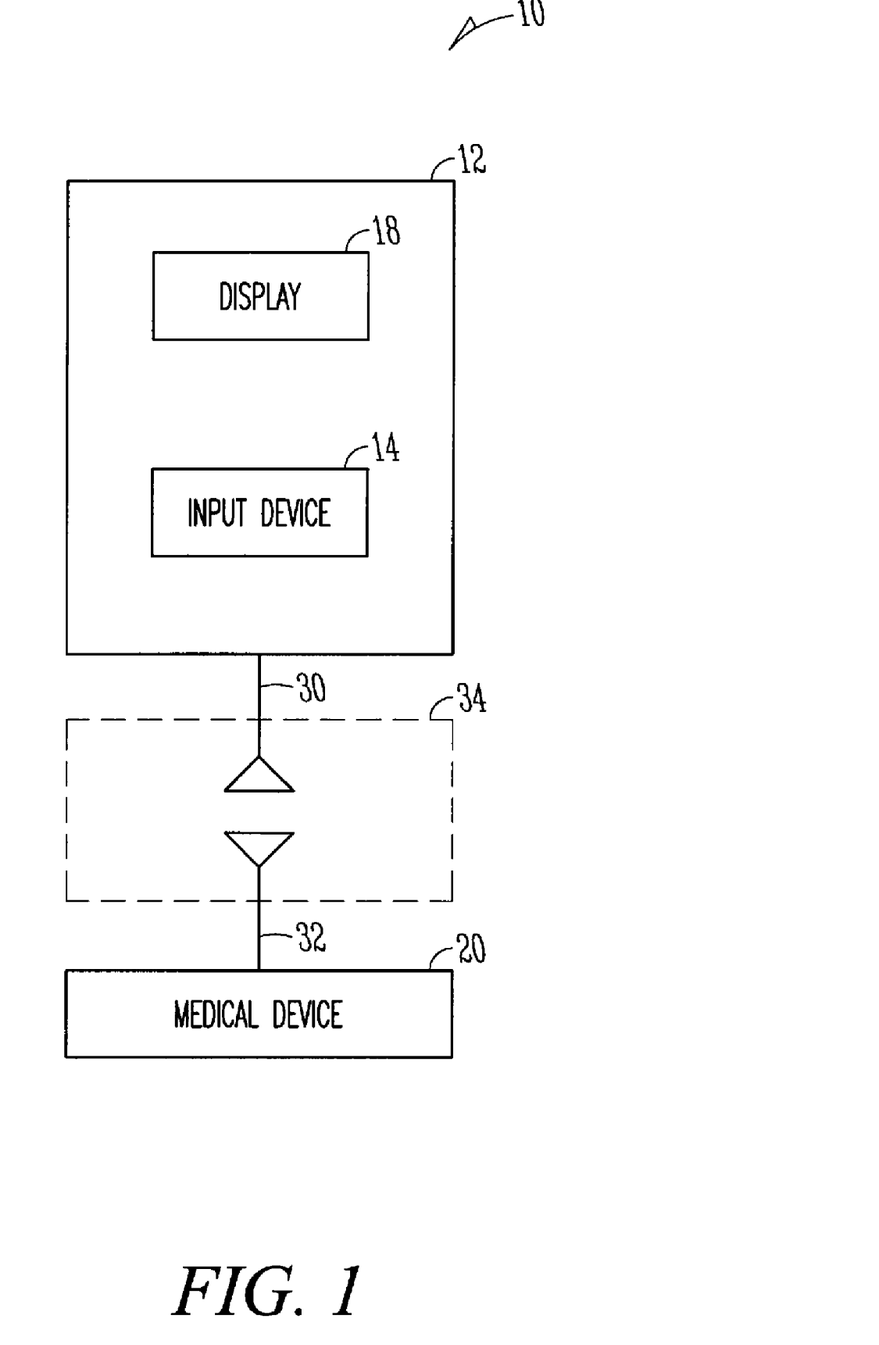
FIG. 1 is an embodiment of an implantable cardiac defibrillator implanted into a heart of a patient, from which portions have been removed to show detail.

FIG. 1 illustrates a medical device system 10 including a medical device programmer 12 and a medical device 20. The programmer 12 includes a processor, memory and a program module for controlling an improved graphical user interface feature that allows a user to adjusts rate thresholds while graphically illustrating the relationship between the rate thresholds the user changed and rate thresholds that are automatically changed by the programmer in response to the rate threshold adjustments made by the user. The programmer 12, illustrated in FIG. 2 also includes an input device 14 and a display 18 and is connected to a medical device via communications link 34, as shown in FIG. 1. In the present embodiment, the communications link 34 is established by the programmer's telemetry system 30 and the medical device's telemetry system 32. In one embodiment, the medical device system is an implantable shock therapy system. An example of such a system is shown in FIG. 3. Medical device 20 generally includes its control unit and implantable leads 22 and 24, coupled to the medical device 20. The leads 22 and 24 are, in turn, introduced into the heart 50, as described below. As also described in more detail below, the medical device 20 may be implanted or may be used as an external device.

The implantable leads 22 and 24 may comprise elongated bodies, having a proximal end 1028 and 32, respectively, and a distal end 60 and 62, respectively. The implantable leads 22 and 24 may include one or more acceleration sensor units 64 and 66, respectively, and may further include one or more pacing/sensing electrodes 68 and 70, respectively. The electrodes 68 and 70 can be used to sense electrical activity or provide electrical stimulation to the heart tissue adjacent to the electrodes.

Each lead 22 and 24 and has an inner lumen 25 and 27, and the acceleration sensor units 64 and 66 may be positioned within the lumens 25 and 27 of each lead. A suitable lead for this purpose is the easy track from Guidant Corporation. Suitable miniaturization accelerometers having a diameter of approximately 1 millimeter available from Ball Semiconductor, Inc. (see U.S. Pat. No. 6,197,610) and others, and these miniaturization accelerometers may be positioned within the inner lumen of the easy track lead and positioned adjacent the lead electrode after the lead has been properly positioned on or within the heart 50. Accelerometer(s) may be positioned in the lumen of the lead within the coronary sinus vein, if desired, thereby minimizing the invasiveness of the accelerometer implantation.

Figure 2:
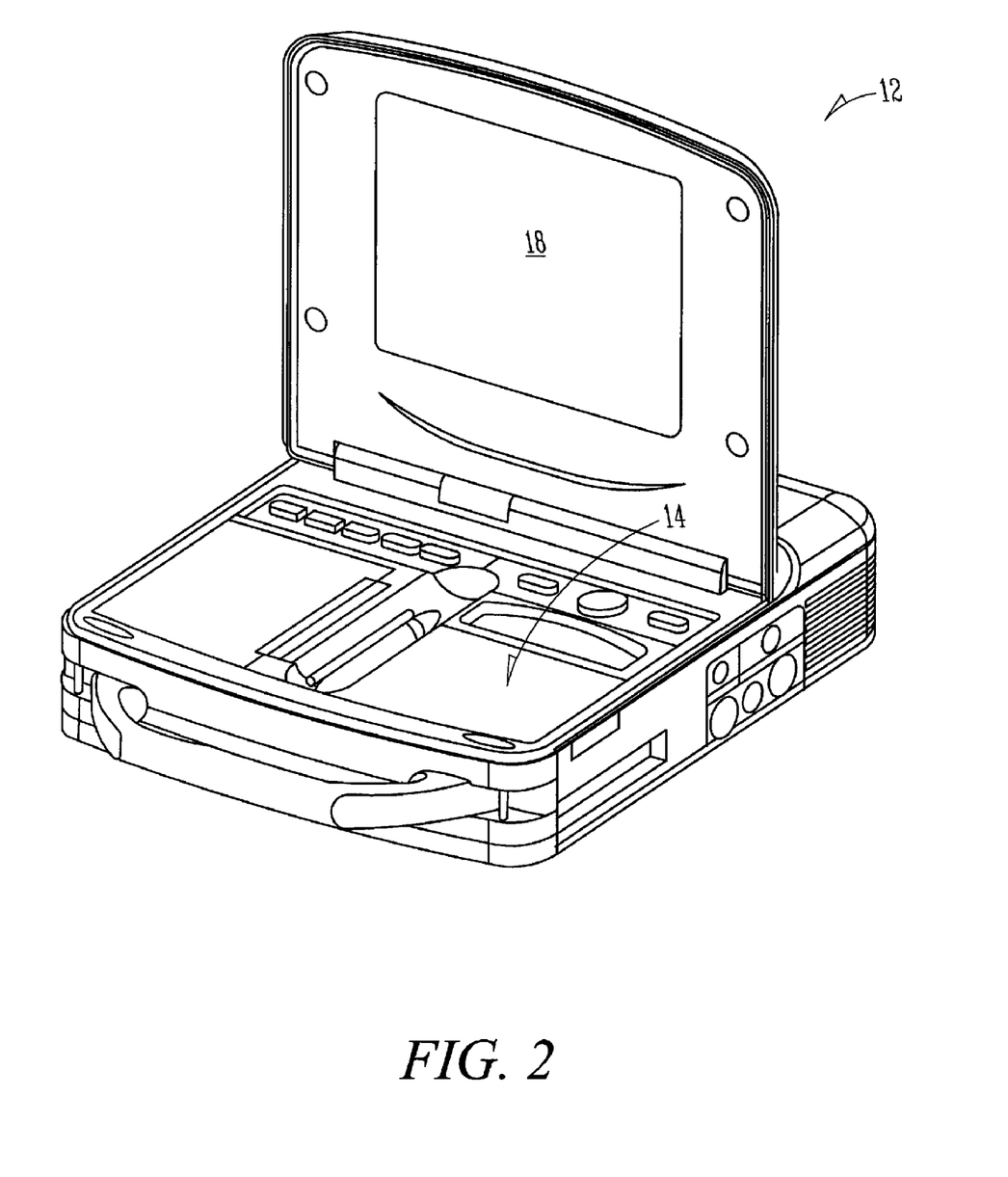
FIG. 2 illustrates a perspective view of an external programming unit according to one embodiment of the present invention that is used for communicating with the defibrillator of FIG. 1.
Figure 3:
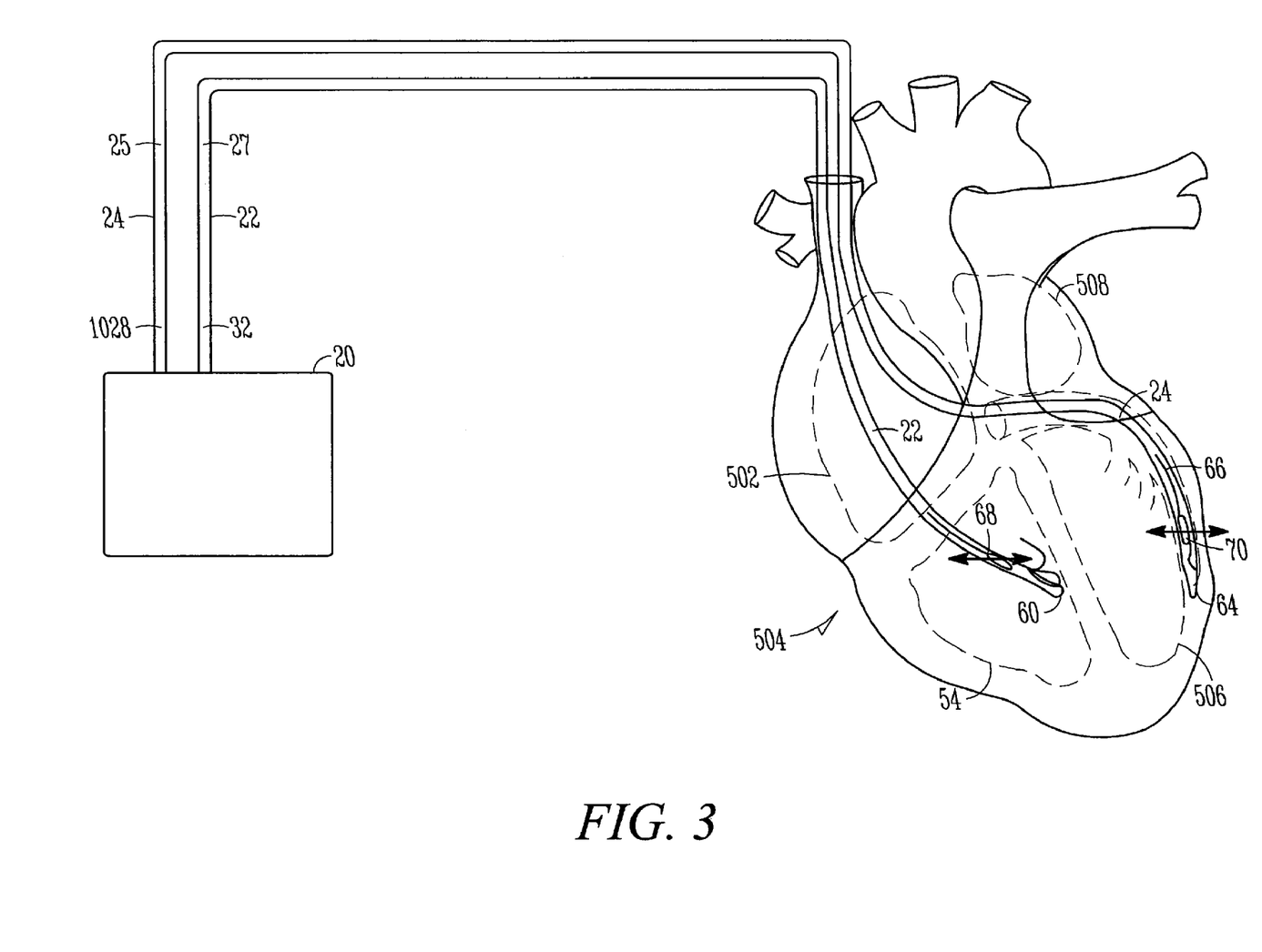
FIG. 3 illustrates one embodiment of an implantable cardiac defibrillator medical device system according to the present invention.

As illustrated in FIG. 2, the programmer 12 includes an input device 14 such as a touch screen pen or mouse, a display 18 and a telemetry system. Features and threshold parameters selected or programmed by physicians into programmer 12 are communicated through telemetry link 30 to the medical device 20 via communication link 32, as illustrated in FIG. 1. The medical device 20 controls how shock and pacing therapy are applied to the patient's heart.

Programmer 12 includes an automatic responsive adjustment function that adjusts related rate threshold parameters of CRM devices while graphically illustrating the relationship between the rate thresholds adjustments on the programmer display 18. The method implemented by programmer 12 provides a user with a means to graphically modify rate thresholds while the programmer itself processes each rate threshold change and automatically modifies related parameters that need to be changed in order to prevent conflicts among related parameters when changes are made.

In one embodiment, the programmer's automatic responsive adjustment function and an interactive programming feedback feature are designed to assist the user in programming the medical device appropriately. In one such embodiment, a set of rules governs the number of possibilities that the various parameters may be programmed to. The rules ensure that incompatibilities among features are identified and prevented and that programming conflicts cannot exist. In one such embodiment, if a user attempts to program a parameter in such a way that may cause incompatibility among features, the programmer 12 automatic responsive adjustment function and interactive programming feedback feature automatically modifies related parameters that need to be changed in order to prevent conflicts in the parameters. In addition, because the programming interface is graphical, the programming interface provides a visual indication on the respective programmer display 18 that informs the user of the changes being made to parameters being changed by the user. It also provides a visual indication on the respective display 18 that informs the user of the automatic changes that occur with related parameters automatically modified in response to the changes being made to selected parameters by the user. The programmer automatically causes changes in related parameters so that the medical device parameter sets remain clear of conflicts.

In some instances, parameter modifications that may cause programming conflicts are not automatically modified by the programmer automatic responsive adjustment function. Under this circumstance, the interactive programming feedback function provides a visual indication on the respective display that informs the user of the programming conflict between parameters.

Figure 4:
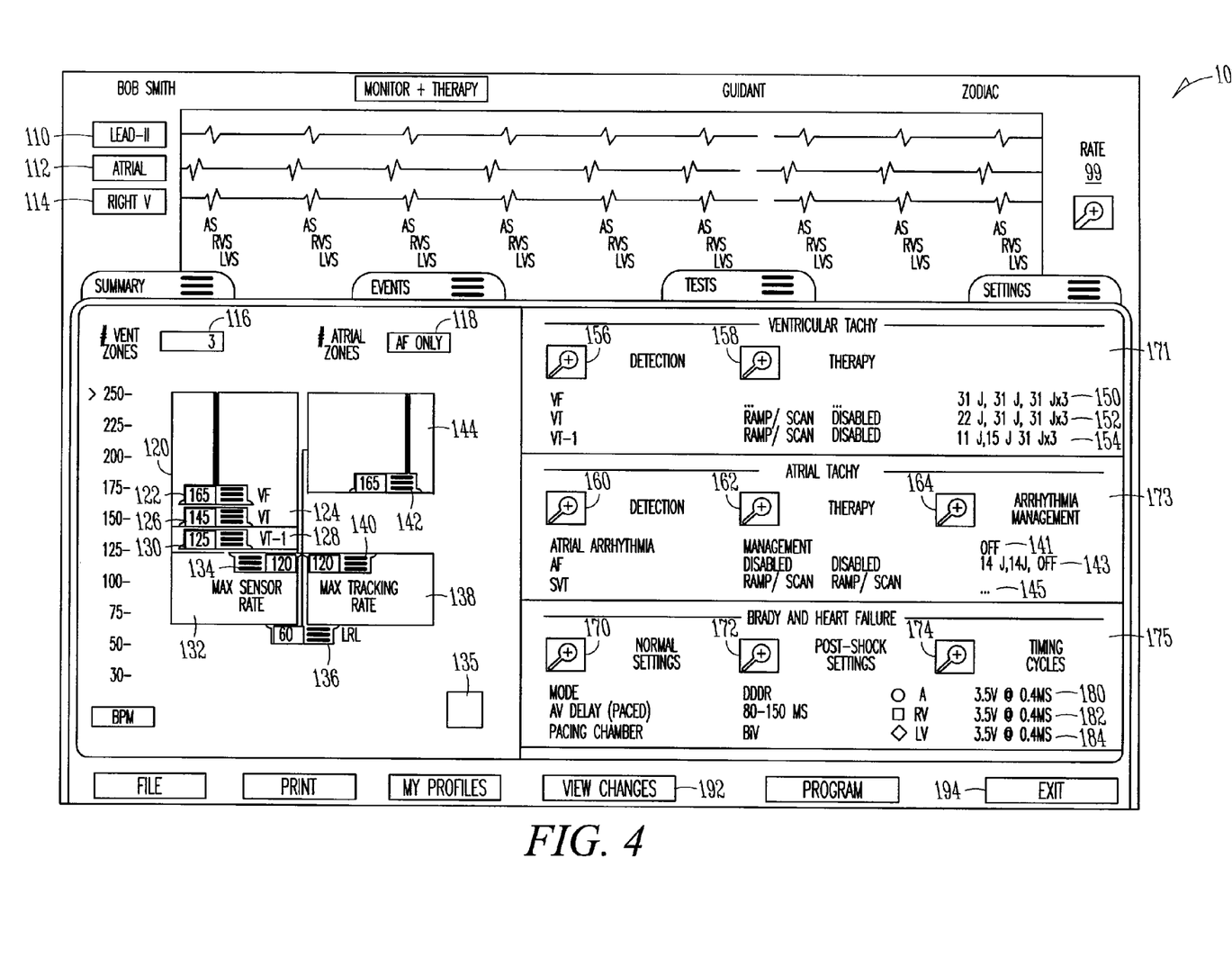
FIG. 4 illustrates one embodiment of a display of a graphical user interface of the external programming unit of FIG. 3 for use in setting and adjusting rate thresholds of an implantable cardiac defibrillator.

A graphical user interface display, which includes the automatic responsive adjustment function and interactive programming feedback feature may be used to set and adjust rate thresholds in ICDs and defibrillators, is shown in FIG. 4. The display shown in FIG. 4 is geared toward the defibrillator system shown in FIG. 1 but can be generalized to control any medical device 20. In the embodiment shown in FIG. 4, the graphical user interface display illustrates that the programmer interface includes seven rate grabbers, Ventricular Fibrillation (VF), Ventricular Tachycardia (VT), Ventricular Tachycardia (VT-1), Atrial Fibrillation (AF), Maximum Sensor Rate (MSR), Maximum Tracking Rate (MTR) and Lower Rate Limit (LRL). Of the seven rate grabbers, three of them are in the ventricle zone (VF, VT, VT-1) and one of them AF is in the atrial zone. In this embodiment, the three ventricular zones (VF, VT, VT-1) and the single atrial zone (AF) are tachyarrythmia zones. The graphical user interface 100 allows the number of zones in the ventricles to be modified and selectively toggled between single zone, dual zone and three zones. This feature is accomplished by the interactive ventricle zone button 116, which allows for the selection of the number of ventricle zones ranging from one to three. In the present embodiment, a single zone ventricle configuration would comprise a VF zone, and a dual zone ventricle configuration would comprise VF and VT zones. It is to be understood that the invention can use any number of rate grabbers. For example, an alternative embodiment may include more or less than seven rate grabbers. If eight rate grabbers are used in an alternative embodiment, the seven rate grabbers previously identified and are utilized along with an AT rate grabber.

Interface For Setting and Adjusting Rate Thresholds

As illustrated in FIG. 4, each ventricular zone is identified on display 100 by colored windows 120, 124, and 128, which are all different colors. Colored window 120 represents the VF zone. Colored window 124 represents the VT zone, and colored window 128 represents the VT-1 zone. Adjacent to the edge of each colored window 120, 124, and 128 are parameter slide controllers 122, 126 and 130. Parameter slide controllers 122, 126 and 130 are the graphical control mechanisms that the system user engages to control threshold settings for VT-1, VT and VF. In the embodiment shown in FIG. 4 the threshold rate for VT-1 is 125 bpm, the threshold rate for VT is 145 BPM and the threshold rate for VF is 165 BPM. The threshold rates for VT-1, VT and VF (125, 145 and 165) are illustrated in the rate windows on parameter slide controllers 122, 126 and 130. The rate windows of the slide controllers (VT) 122, (VF) 126, (VT-1) 130, (AF) 142, (MSR) 134, (MTR) 140, and (LRL) 136 has a white background that indicates to the user that the threshold rates illustrated in the slide controller rate windows are threshold rates currently programmed in the medical device. The threshold rates within the rate windows on parameter slide controllers 122, 126 and 130 are modified by sliding the parameter slide controllers 122, 126 and 130 up and down vertically. When threshold rates are adjusted, the background of the slide controller rate window changes to a different color to indicate that the threshold rate illustrated in the window is a proposed rate that has not be programmed. In the present embodiment, the background of the slide controller rate window changes to green to illustrate that a threshold rate adjustment has been made. It is to be understood that the background or the actual text within the slide controller rate window may be changed to any color so long as the colors indicate that the rates have been adjusted. In addition to the background of the slide controllers (VT) 122, (VF) 126, (VT-1) 130, (AF) 142, (MSR) 134, (MTR) 140, and (LRL) 136 changing to a different color when the threshold rates for VT, VF, VT-1, AF, MSR, MTR and LRL are adjusted, the threshold rates for VT, VF, VT-1, AF, MSR, MTR and LRL programmed into the medical device (the threshold rate displayed in the slide controller prior to modification) are displayed in parenthesis in close proximity to the slide controller to illustrate to the user the threshold rate currently programmed into the medical device.

Movement of parameter slide controllers 122, 126 and 130 vertically upward causes threshold settings for VT-1, VT and VF to be increased and such increase is reflected within the rate control windows on the parameter slide controllers 122, 126 and 130. Movement of parameter slide controllers 122, 126 and 130 vertically upward also causes the size of the colored windows 120, 124 and 128 to be decreased or remain the same. Movement of parameter slide controllers 122, 126 and 130 vertically downward causes threshold settings for VT-1, VT and VF to be decreased and such decrease is reflected within the rate windows on the parameter slide controllers 122, 126 and 130. It also causes the size of the colored windows 120, 124 and 128 to be increased or remain the same. If the parameter slide controller 130 is adjusted by the system user or automatically in response to the automatic responsive adjustment function whereby the threshold rate of VT-1 is reduced to a rate that is within a predetermined range of the maximum sensor rate or maximum tracking rate thresholds displayed, the automatic responsive adjustment function causes automatic adjustment of the maximum sensor rate and or maximum tracking rate via parameter slider controllers 134 and 140. In the present embodiment, the predetermined range is 5 Bpm in accordance with programmer rules that require a range of at least 5 Bpm between the threshold rate of VT-1 and the thresholds for the maximum sensor rate and maximum tracking rate. It is to be understood that the predetermined range may vary and is dependent upon the level of safety the programmer rules are implementing into the automatic responsive adjustment function.

It is to be understood that the predetermined range may be set at any range necessary for the system to accomplish the automatic responsive adjustment function. Parameter slide controllers 134 and 140 are automatically moved to adjust the maximum sensor rate and or maximum tracking rate thresholds to rates that are consistent with the rules and do not cause parameter conflicts. In the embodiment illustrated in display 100, the maximum sensor rate and or maximum tracking rate thresholds are adjusted so that the threshold rates are at least 5 Bpm less than the threshold rate of VT-1. If adjustment of the maximum sensor rate and or maximum tracking rate thresholds downward causes the maximum sensor rate and or maximum tracking rate thresholds to be within a predetermined range of the lower rate limit, the automatic responsive adjustment function adjusts the lower rate limit threshold downward. In the present embodiment, the predetermined range is 15 Bpm in accordance with programmer rules that require a range of at least 15 Bpm between the lower rate limit threshold and the thresholds for the maximum sensor rate and maximum tracking rate. It is to be understood that the predetermined range may vary and is dependent upon the level of safety the programmer rules are implementing into the automatic responsive adjustment function.

During movement of parameter slide controllers 122, 126 and 130 to adjust the threshold settings for VT-1, VT and VF, if an attempt is made to change one of the threshold settings for VT-1, VT and VF to a level where the difference between setting rates of VT-1 and VT and VT and VF have ranges that are less than minimum ranges set by programmer rules that control engagement of the automatic responsive adjustment feature, the automatic responsive adjustment feature engages. In the present embodiment, the minimum ranges set for difference between the threshold setting rates of VT-1 and VT and VT and VF is 20 beats per minute (Bpm). The automatic adjustment feature engages upon the adjustment of threshold settings for VT-1, VT and VF via movement of parameter slide controllers 122, 126, 130 vertically upward or downward, when the resulting difference between VT-1 and VT and/or VF and VF is less than 20 Bpm.

By way of example, the automatic responsive adjustment feature engages as a result of the threshold level for VT-1 being increased to a level that would cause the difference in threshold levels between VT-1 and VT to be smaller than 20 Bpm. When the automatic responsive adjustment feature engages, it causes VF to increase to a level wherein the threshold level for VF is equal to VT plus the minimum range set by program rules. Or, in the present embodiment, VF is equal to the new threshold level set for VT plus 20 Bpm. In addition, the automatic responsive adjustment feature engages as a result of the threshold level for VF being lowered to a level that would cause the difference in threshold levels between VT and VF to be smaller than the minimum range set by programmer rules that control engagement of the responsive adjustment feature (20 Bpm). When the automatic responsive adjustment feature engages, it causes VT to be automatically lowered to a level wherein the threshold level for VT is 20 Bpm lower than the new threshold level for VF. The automatic responsive adjustment feature also engages as a result of the threshold level for VT-1 being increased to a level that would cause the difference in threshold levels between VT-1 and VT to be smaller than the minimum range set by programmer rules that control engagement of the automatic responsive adjustment feature (20 Bpm). When the automatic responsive adjustment feature engages, it causes VT to increase to a level wherein the threshold level for VT is 20 Bpm greater than the new threshold level for VT-1. In addition, the automatic responsive adjustment feature engages as a result of the threshold level for VT being lowered to a level that would cause the difference in threshold levels between VT-1 and VT to be smaller than the minimum range set by programmer rules that control engagement of the automatic responsive adjustment feature (20 Bpm). When the automatic responsive adjustment feature engages, it causes VT-1 to be automatically lowered to a level wherein the threshold level for VT-1 is 20 Bpm lower than the new threshold level for VT.

The atrial zone illustrated in display 100 is also shown to have threshold rates defined by a colored window 144 and a parameter slide controller 142. Colored window 144 represents the AF zone. Adjacent to the edge of colored window 144 is a parameter slide controller 142 that the user engages to control the threshold settings for AF. As illustrated in FIG. 4, the threshold rate for AF, as illustrated in the rate window of parameter slide controller 142, is 170 Bpm. The AF threshold may be modified by moving the parameter slide controller 142 upward to increase the threshold level and downward to decrease the threshold level. If the parameter slide controller 142 is adjusted by the system user and the resulting threshold rate of AF is reduced to a threshold rate that is within a predetermined range of the maximum sensor rate or maximum tracking rate thresholds displayed, the automatic responsive adjustment feature engages and causes automatic adjustment of the maximum sensor rate and or maximum tracking rate via parameter slider controllers 134 and 140 so that the AF threshold rate remains at least at a predefined level as defined by program rules higher than the maximum sensor rate and maximum tracking rate. In the present embodiment, the predetermined range is 5 Bpm, and in accordance with programmer rules there is a required range of at least 5 Bpm between the resulting threshold rate of AF and the resulting maximum sensor rate and maximum tracking rate. Parameter slide controllers 134 and 140 are automatically moved to adjust the maximum sensor rate and or maximum tracking rate thresholds to rates that are consistent with the rules so as to prevent parameter conflicts. In the embodiment illustrated in display 100, the maximum sensor rate and or maximum tracking rate thresholds are automatically adjusted downward so that the threshold rates are at defined level less than the threshold rate of AF. In the present embodiment, the maximum sensor rate and or maximum tracking rate thresholds are automatically adjusted downward so that the threshold rates are at least 5 Bpm less than the threshold rate of AF. If adjustment of the maximum sensor rate and or maximum tracking rate thresholds downward via movement of parameter slide controllers 134 and 140 or adjustment of the lower rate limit upward via movement of parameter slide controller 136 causes the maximum sensor rate and or maximum tracking rate thresholds to be within a range defined by programmer rules of the lower rate limit threshold rate, the automatic programming function adjusts the lower rate limit threshold downward or the maximum sensor rate and maximum tracking rate upward, maintaining a threshold range in accordance with the range defined by the programmer rules between the lower rate limit and the maximum sensor rate and maximum tracking rate. In this embodiment the range set by programmer rules is 15 Bpm. The programmer rules require a range of at least 15 Bpm between the lower rate limit threshold and the thresholds for the maximum sensor rate and maximum tracking rate.

When the AF threshold level is increased, the size of colored window 144 becomes smaller. When the AF threshold level is decreased, the size of the colored window 144 becomes larger. The graphical user interface 100 further allows the number of atrial zones to also be modified and selectively toggled between single zone and dual zones. The present embodiment is a single zone atrial configuration that includes an AF zone only. Alternatively, engaging interactive atrial zone button 118 allows for the selection of two alternative dual zone sets. A first atrial zone set being comprised of AF and AT and a second atrial zone set being comprised of AF Rhythm and AT.

The graphical user interface 100 also provides rate grabbers for Brady threshold rates for the ventricle and atrial zones. The Brady threshold rates are comprised of the maximum sensor rate, maximum tracking rate and lower rate limit. The maximum sensor rate 132, illustrated by a first edge of the window 132, has a parameter slide controller 134 adjacent the first edge. The parameter slide controller 134 includes a rate window that also illustrates a maximum sensor threshold rate. The threshold rate illustrated within the rate window of parameter slide controller 134 may be the rate currently programmed in the medical device, if the background of the rate window is white, or it would reflect a new threshold that has not be transmitted to the medical device if the background of the rate window is green. It is to be understood that the feature of changing the background of the rate window of parameter slide controllers applies to all slide controllers of this invention, and is not to be limited by colors being used. The concept of advising the user as to whether the parameter illustrated in the rate window is already programmed in the medical device or one that may be programmed in the feature or of the important features. The maximum tracking rate 140, illustrated by a first edge of the colored window 138, has a parameter slide controller 140 adjacent the first edge. The parameter slide controller 140 includes a rate window that also illustrates a maximum tracking threshold rate. The lower rate limit is illustrated by a parameter slide controller 136 that is adjacent a second edge of the maximum sensor rate colored window 132 and a second edge of the maximum tracking rate colored window 138. The Brady threshold upper rate limit is the higher threshold rate of the maximum sensor rate and maximum tracking rate, reflected in the first edge or in the rate window of parameter slide controllers 134 and 140.

As illustrated in FIG. 4, the maximum sensor rate 132 and the maximum tracking rate 138 are both 120 Bpm. Both the maximum sensor rate 132 and the maximum tracking rate 138 may be increased or decreased by sliding the parameter slide controllers 134 and 140 vertically upward or downward. The programmer rules that control engagement of the automatic responsive adjustment feature governs interaction of maximum sensor rate 132 and maximum tracking rate 138 and controls the range within which the maximum sensor rate 132 and maximum tracking rate 138 may be adjusted. In this embodiment, the maximum sensor rate 132 may be increased or decreased by sliding the parameter slide controller 134 vertically upward or downward until it reaches a maximum or minimum defined by program rules. In this embodiment, the maximum sensor rate may be increased up to a point at which the threshold rate is at least 5 Bpm less than VT-1 (125 Bpm) or, in the present embodiment 120 Bpm. Accordingly, in the embodiment illustrated in FIG. 4, the maximum sensor rate parameter slide controller 134 may not be adjusted upward to increase the maximum sensor rate as it is already at its highest level possible within the program rules. The automatic responsive adjustment feature, in accordance with the rules, will not allow the maximum sensor rate to be increased because an increase of the maximum sensor rate to a threshold rate that is within 5 BP of the threshold rate of VT-1 would cause parameter conflicts. To prevent such conflicts, the automatic responsive adjustment feature prevents such an adjustment. Notwithstanding, in an alternative embodiment, wherein the threshold rate of VT-1 has been removed from the display and only two zones VT and VF are illustrated in display 100, the maximum sensor rate could be increased via slider 134 up to 140 Bpm. Upon the maximum sensor rate reaching 140 Bpm, the parameter control slider 134 is not allowed to move upward any further. Under no circumstance does the automatic responsive adjustment feature allow an increase of the maximum sensor rate to adjust the threshold rates of VF, VT and VT-1. The maximum sensor rate may only be increased to a threshold rate that is at least 5 Bpm less than the smaller of the threshold rates for VF, VT and VT-1. The maximum sensor rate may be decreased to a minimum level set by program rules by moving the parameter slide controller 134 downward.

Similar to the maximum sensor rate, the maximum tracking rate 138 may also be increased or decreased by sliding the parameter slide controller 140 vertically upward or downward. In this embodiment, the maximum tracking rate may be increased up to a point at which the threshold rate is at least 5 Bpm less than VT-1(125 Bpm) or, in the present embodiment 120 Bpm. Accordingly, in the embodiment illustrated in FIG. 4, the maximum tracking rate parameter slide controller 140 may not be adjusted upward to increase the maximum sensor rate as it is already at its highest level possible within the rules. The automatic responsive adjustment feature, in accordance with the rules, will not allow the maximum tracking rate to be increased because an increase of the maximum tracking rate to a rate that is within 5 Bpm of the threshold rate of VT-1 would cause parameter conflicts. To prevent such conflicts, the automatic responsive adjustment feature prevents such an adjustment. Notwithstanding, in an alternative embodiment, wherein the threshold rate of VT-1 has been removed from the display and only two zones VT and VF are illustrated in display 100, the maximum tracking rate could be increased via slider 140 up to 140 Bpm. Upon the maximum tracking rate reaching 140 Bpm, the parameter control slider 140 is not allowed to move upward any further. Under no circumstance does the automatic responsive adjustment feature allow an increase of the maximum tracking rate to adjust the threshold rates of VF, VT and VT-1. The maximum tracking rate may only be increased to a threshold rate that is at least 5 Bpm less than the smaller of the threshold rates for VF, VT and VT-1. The maximum tracking rate may be decreased to a minimum level set by program rules by moving the parameter slide controller 140 downward.

In the embodiment illustrated in display 100, the maximum sensor rate and maximum tracking rate colored windows 132 and 138 may decreased by sliding lower rate limit parameter slide controller 136 upward until the lower rate limit reaches 105 Bpm. This reflects that the maximum sensor rate and maximum tracking rate range colored windows 132 and 138 are only 15 Bpm each. The programmer rules require a range of at least 15 Bpm between the lower rate limit threshold and the thresholds for the maximum sensor rate and maximum tracking rate. Accordingly, in the embodiment illustrated in FIG. 4, the lower rate limit parameter slide controller 136 may not be adjusted upward to increase the lower rate limit threshold as it is already at its highest level possible within the rules. The automatic responsive adjustment feature, in accordance with the rules, will not allow the lower rate limit threshold to be increased because an increase of the lower rate limit threshold to a threshold rate that is less than 15 Bpm would cause parameter conflicts. To prevent such conflicts, the automatic responsive adjustment feature prevents such an adjustment. Notwithstanding, in an alternative embodiment, wherein the threshold rate of VT-1 has been removed from the display and only two zones VT and VF are illustrated in display 100, the lower rate limit threshold could be increased via parameter control slider 136 up to 125 Bpm. Moving of lower rate limit parameter control slider 136 up to 125 Bpm causes the automatic responsive adjustment feature to automatically adjust the maximum sensor rate and maximum tracking rate thresholds upward via automatic movement of the maximum sensor rate and maximum tracking rate parameter slide controllers 134 and 140. Upon the maximum sensor rate and maximum tracking rate reaching threshold rates of 140 Bpm, the parameter control sliders 134 and 140 are not allowed to move upward any further. Under no circumstance does the automatic responsive adjustment feature allow an increase of the maximum tracking rate to adjust the threshold rates of VF, VT and VT-1. The maximum tracking rate may only be increased to a threshold rate that is at least 5 Bpm less than the smaller of the threshold rates for VF, VT and VT-1. The maximum tracking rate may be decreased to a minimum level set by program rules by moving the parameter slide controller 140 downward.

Display 100 includes colored display windows 120, 124, 128, 132, 138, 144, that are comprised of at least three distinct colors, one color for the atrial, one for the ventricle and one for Brady. In the present embodiment, the colored display windows 120, 124, and 128 for ventricle zones VF, VT and VT-1 are comprised of different shades of a color to reflect that there are three separate and discrete zones in the ventricle. In an alternative embodiment in which the Atrial Zone is comprised of two zones, demarcated by atrial tachyarrhythmia rate thresholds AF and AT, AF and AT are comprised of different shades of a color to reflect that there are two separate and discrete zones.

On the right-hand side of display 100, therapy summary areas for ventricular tachy therapy, atrial tachy therapy and Brady therapy are illustrated in summary areas 171, 173 and 175. Ventricular tachy summary area 171 displays the patient scheme, mode and rate for each of the three zones VF, VT and VT-1 at 150, 152 and 154. Additional ventricular tachy parameter settings may be viewed and changed by selecting the detection or therapy buttons 156 and 158.

Atrial tachy summary area 173 illustrates the pacing mode and rates within the atrial zones. In the embodiment illustrated in display 100, the atrial tachy therapy summary illustrates the pacing modes and rates within the atrial zones 141, 143 and 145. Additional atrial tachy parameter settings may be viewed and changed by selecting the detection management button 160, therapy management button 162 or arrhythmia management button 164. The Brady therapy summary area 175 illustrates the normal and post-shock Brady cardio modes, rates, and outputs 180, 182 and 184. Additional Brady cardio parameters settings may be viewed and changed by selecting the Brady cardio normal settings button 170, the post shock settings button 172, and the timing cycles button 174.

In the embodiment shown in FIG. 4, the ECG display 110, 112 and 114 is always visible. The ECG display 110, 112, 114 shows real time surface ECG traces, as well as real-time electro grams, which are useful in ascertaining system performance.

In one embodiment, real-time electro grams can be transmitted from the pace/sense or shocking electrodes to evaluate lead system integrity such as lead fractures, insulation breaks, or dislodgments.

As illustrated in FIG. 4, the graphical user interface display 100 illustrates the threshold settings in beats per minute in accordance with the scale positioned in proximity to the colored windows 120, 124, and 128 and parameter slide controllers slide controllers 122, 126, 130, 142, 134, 140, and 136 along the left side of graphical user interface 100. The scale along the left side of graphical user interface 100 may be modified and illustrated in time as milliseconds by engaging the scale modification button 135. Engaging the scale modification button also changes the values inside the slide controller windows to be reflective of intervals instead of rate. FIG. 4 illustrates display 100 wherein the scale modification button 135 has been engaged and the values inside the slide controller windows are reflective of intervals.

Interface For Setting, Adjusting and Visualizing Device Timing Behavior

Figure 5:
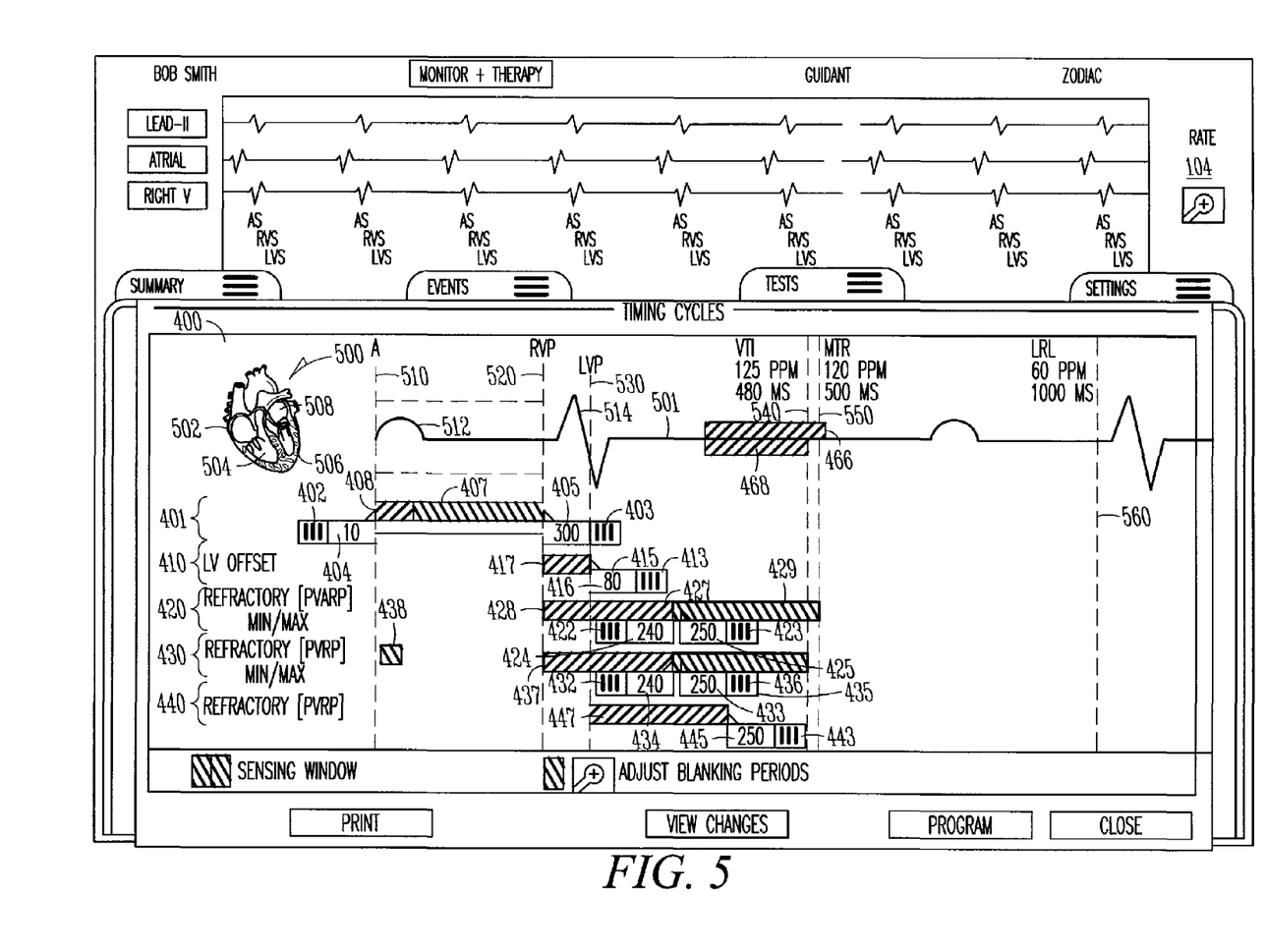
FIG. 5 illustrates one embodiment of a display of a graphical user interface of the external programming unit of FIG. 3 for use in adjusting and visualizing device timing of an implantable cardiac defibrillator.
Figure 6:
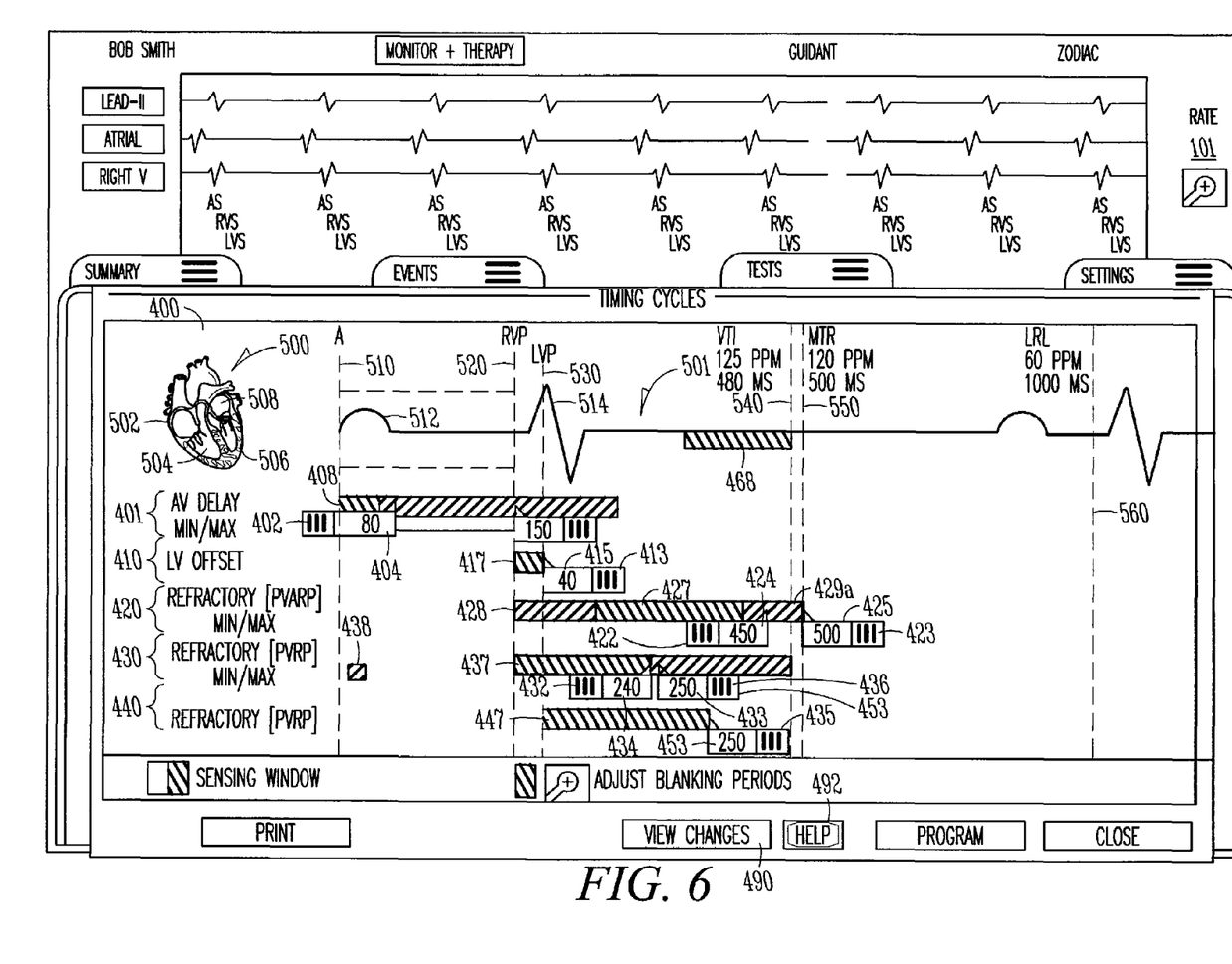
FIG. 6 illustrates one embodiment of a display of a graphical user interface of the external programming unit of FIG. 3 for use in adjusting and visualizing device timing of an implantable cardiac defibrillator.

In order to understand and analyze a cardiac cycle in a heart, it is common to break the cardiac cycle down into its composite parts. Display 400 assists in the understanding of the cardiac cycles of the heart by illustrating the respective timing intervals of the cardiac cycle and how the timing intervals interrelate with each other.

Referring to FIGS. 5 and 6, is another illustration of a graphical user interface display 400 wherein the programmer utilizes the automatic responsive adjustment feature. Display 400 is used for setting, adjusting and graphically visualizing device timing behavior and the relationship between different timing parameters. It also prevents certain timing behavior in an implantable medical device from being set to an unsafe or undesirable condition. It also provides the programmer user with the ability to graphically communicate how cardiac conditions relate to particular parameters as the user adjusts parameters such as Atrioventricular delay (AV delay), left ventricular offset (LV offset), post-ventricular atrial refractory period (PVARP) right ventricular refractory period (RVRP), and left ventricular refractory period (LVRP). It also allows the programmer user to graphically resolve potentially unsafe conditions and undesirable states resulting from the adjustment of parameters. It further allows the user to visualize the graphic relationship between timing parameters such as AV delay, LV offset, PVARP, RVRP and LVRP while facilitating the user's ability to graphically adjust the atrial and ventricular timing settings using parameter control sliders. When the timing parameters are adjusted by the parameter slide controllers, the timing behavior including sensing windows and blanking periods will also be graphically displayed. Display 400 also uses color codes to illustrate the relationship between different atrial and ventricular timing settings and the status of the certain parameter changes. With certain parameter changes, the change is illustrated with a green background because it is a safe. Other parameter changes are illustrated with a yellow background to illustrate that the proposed change are undesirable and with a red background to illustrate that the proposed changes are unsafe. Yellow is to warn the user and red is to indicate that an error will occur if an attempt is made to program the parameters illustrated. Under these circumstances, the programmer automatically indicates recommended changes to overcome the undesirable or unsafe conditions.

Display 400 includes an AV delay area 401, an LV offset area 410, a PVARP display area 420, an RVRP display area 430 and an LVRP display area 440. Each display area, including LV delay area 401, an LV offset area 410, an PVARP display area 420, an RVRP display area 430 and an LVRP display area 440, illustrates timing settings and includes parameter slide controllers for adjusting the timing settings graphically. The AV display area 401 illustrates the timing setting associated with the AV delay timing interval and includes a graphical user interface for adjusting the minimum and maximum values for AV delay. Although not to scale, it also includes a graphical representation of the AV delay timing cycle in relation to the LV offset, PVARP, RVRP and LVRP timing settings. The adjustments to AV delay are accomplished by movement of parameter slide controllers 402 and 403 to the appropriate timing settings. The adjusted or programmed parameters of the AV delay are illustrated in the parameter slide controller rate windows 404 and 405.

The atrial pulse indicator line 510 illustrates the beginning of the AV delay period, which ends at the Right Ventricular Pulse (RVP) indicator line 520. The graphical representation of the AV delay timing cycle is further reflected in the adjustment guide 407 which is a graphical display of the AV delay timing cycle shown in relation to the timing cycles for, LV offset, PVARP, RVRP and LVRP. When it is desired to adjust the minimum and or maximum rates for the AV delay, parameter slide controllers 402 and 403 are moved horizontally along the adjustment guide 407. Movement of parameter slide controllers 402 and 403 causes the parameters illustrated within the parameter slide controller rate windows 404 and 405 to be adjusted. Movement of parameter slide controller 403 also causes the movement of the Right Ventricular Pulse (RVP) indicator line 520. The RVP indicator line 520 is representative of the beginning of the right side of the timing interval. It may be reflective of a sensed ventricular event (R wave) or a ventricular pace.

It can be seen in display 400 that the AV delay minimum illustrated in the parameter slide controller rate window 404 in display 400 is 10 milliseconds. The AV delay maximum has been adjusted to 300 milliseconds by movement of parameter slide controller 403. The user is automatically advised that the 300 milliseconds illustrated in the parameter slide controller rate window 405 is not the AV delay maximum parameter that is programmed into the medical device because the background of the rate window 405 is green. Whenever the user of the programmer's graphical user interface adjusts parameters within the parameter slide controllers, the background of the parameter slide controller rate window changes to another color. In the present embodiment, the background is white when the parameter within the parameter slide controller rate window reflects the value previously programmed to the medical device. The background is green when the parameter within the parameter slide controller rate window is a non-conflicting parameter that has not been programmed to the medical device. The background is red when the parameter within the parameter slide controller rate window is a conflicting parameter with another parameter. In instances where the parameter slide controller rate window displays a parameter that conflicts with other parameters and thereby may cause an unsafe condition, the program rules prevent the transmission of such a parameter to the medical device. As illustrated in FIG. 6, display 400 also provides the user with the ability to view the changes by engaging the view changes button 490 and the ability to seek help regarding the conflicting parameters by engaging the help button 492.

Regarding the maximum AV delay, the medical device is sensing for a P wave from the atrial pulse indicator line 510 following the occurrence of the Atrial pulse 512 up to Right Ventricular Pulse (RVP) indicator line 520 or for up to 300 milliseconds. If a P wave is sensed prior to completion of 300 milliseconds, the sensed ventricular event is used as a basis for all other interval timing. That sensed event acts as the beginning of the timing intervals for the LV offset, the PVARP, RVRP and LVRP refractory periods, and the overall cardiac cycle intervals which end at the lower rate limit (LRL). Because all timing is based off ventricular to ventricular events, if something is sensed within the AV delay interval, or in the example illustrated in display 400 within 300 milliseconds, then that is the beginning of a new cycle. If a ventricular pulse is not sensed within 300 milliseconds, then the medical device will send a pulse to the right ventricle of the heart at 300 milliseconds as illustrated by Right Ventricular Pulse (RVP) indicator line 520. Under this circumstance, the Right Ventricular Pulse (RVP) indicator line 520 is used as the base timing for all other interval timing because an R wave will not have been sensed within the AV delay timing period or within 300 milliseconds. The minimum AV delay, as illustrated in the AV delay display area 401 is 10 milliseconds. The minimum AV delay corresponds to the maximum tracking rate (MTR) or the maximum sensor rate (MSR), which is 120 pulses per minute or 500 milliseconds. The maximum AV delay corresponds to the lower rate limit (LRL) 60 pulses per minute Ppm or 1000 milliseconds.

The LV offset display area 410 includes an LV offset parameter slide controller 413 and an adjustment guide 417 which provides a visual display of the LV offset timing window. The LV offset parameter slide controller 413 may be moved horizontally forward and backward to increase or decrease the LV offset timing window. Upon movement of the LV offset parameter slide controller 413, the LV offset rate adjusts as illustrated in the LV offset parameter slide controller rate window 415. The Left Ventricular Pace (LVP) indicator 530 line is an indication of the level at which the pacing in the left chamber needs to be offset from the pacing in the right chamber. Parameter slide controller 413 may be adjusted to the left of the Right Ventricular Pulse (RVP) indicator line 520 or to the right of the Right Ventricular Pulse (RVP) indicator line 520. Movement of slide controller 513 to the left of the Right Ventricular Pulse (RVP) indicator line 520 indicates that the LV offset may be set for example at negative timing window, for example negative 40 milliseconds, which is reflective of the concept that the left chamber needs to be paced 40 milliseconds before the right chamber. Accordingly, Parameter slide controller 413 can be adjusted to either side of Right Ventricular Pulse (RVP) indicator line 520. However, timing shall be based off of the Right Ventricular Pace.

Left Ventricular Pulse (LVP) indicator line 530 is the second edge of the LV offset window, which begins at the Right Ventricular Pulse (RVP) indicator line 520 and ends at the Left Ventricular Pulse (LVP) indicator line 530. The actual value of the LV offset in the embodiment illustrated in display 400 is 80 milliseconds. The LV offset value may be modified or adjusted by sliding parameter slide controller 413 from the edge of the Right Ventricular Pulse (RVP) indicator line 520 up to a timing rate allowable within the program rules.

PVARP display area 420 is a post-ventricular atrial refractory period. Refractory periods are defined to make sure that the medical device doesn't sense during inappropriate times. If a natural event occurs, for example, a P wave or an R wave, or the medical device paces, the event may have happened in another chamber. However, some of the event may be sensed in other chambers and the medical device may believe an event has occurred in chambers for which an event has not. When this happens, it is problematic if the medical device reacts to these events. The refractory period makes sure that the medical device is not over sensing and thereby prevents the sensing of events in chambers that the medical device should be ignoring. Even though the medical device may see an event from a first chamber in a second chamber as if it occurred in the second chamber, the medical device will ignore the first chambers event during the refractory period. The chemistry of the heart tissue requires that the tissue receive a time of rest (refractory period) after it squeezes before it can squeeze again. Generally, the heart does not respond during this period. If the heart is not responding because it physically cannot, the medical device should not be responding to sensed events. If the medical device does not ignore those sensed events as the heart does, premature pacing would occur. Refractory periods are periods where the medical device sensing is blinded and the medical device will not pace if it senses an event during the refractory period.

The PVARP refractory period represented by the period from the edge of the Right Ventricular Pulse (RVP) indicator line 520 to the edge of the parameter slide controller 523, is not reflected in display 400 to scale. The actual minimum and maximum PVARP refractory periods are displayed in the parameter slide controller rate windows 424 and 425 of parameter slide controllers 422 and 423. The period from the edge of the parameter slide controller 423 to the maximum tracking rate indicator 550 is the period during which sensing following the right ventricular pace can occur. The period during which sensing can occur is graphically illustrated by changing the background of a portion of adjustment guide 427 to an alternative color or texture, represented in display 400 as white background with diagonal blue lines 429 drawn there though.

The PVARP refractory period is the period that affects sensing in the atrium following a right ventricular pace. Any events that occur within the atrium immediately following the Right Ventricular Pulse (RVP) indicator line 520 all the way to the maximum PVARP will be ignored. Alternatively, if the minimum PVARP is used, anything that occurs immediately following the Right Ventricular Pulse (RVP) indicator line 520 to the minimum PVARP will be ignored. Whether the system user utilizes the minimum or maximum PVARP is dependent upon whether pacing is occurring at the lower rate limit (LRL) 560 or the maximum tracking rate (MTR) 550. If pacing by the medical device is occurring at the lower rate limit (LRL) 560, anything sensed in the atrium between 0 and 250 milliseconds will be ignored. If pacing is based off of the maximum tracking rate (MTR) 550, anything sensed between 0 and 240 milliseconds will be ignored.

RVRP display area 430 is representative of the right ventricular refractory period. It is comprised of the time that the ventricular sensing on the right side is ignoring events following a right ventricular pace represented by Right Ventricular Pulse (RVP) indicator line 520. The RVRP display area 430 includes a blanking period 438, parameter slide controllers 432 and 435 and an adjustment guide 437. The RVIRP refractory period represented by the period from the edge of the Right Ventricular Pulse (RVP) indicator line 520 to the edge of the parameter slide controller 435, is not reflected is display 400 to scale. The actual minimum and maximum RVRP refractory periods are displayed in the parameter slide controller rate windows 433 and 434 and may be adjusted by horizontal movement of parameter slide controllers 432 and 435. The period from the edge of the parameter slide controller 435 to the Maximum Tracking Rate (MTR) indicator 550 is the period during which sensing following the right ventricular pace can occur.

The RVRP refractory period is the period that affects sensing in the right ventricle following a right ventricular pace. Any events that occur within the right ventricle immediately following the Right Ventricular Pulse (RVP) indicator line 520 all the way to the maximum RVRP (represented by the edge of the parameter slide controller 535) will be ignored. Alternatively, if the minimum RVRP (represented by the edge of the parameter slide controller 532) is used, anything that occurs immediately following the Right Ventricular Pulse (RVP) indicator line 520 to the edge of the parameter slide controller 532 will be ignored. Whether the system user utilizes the minimum or maximum RVRP is dependent upon whether pacing is occurring at the lower rate limit (LRL) 560 or the maximum tracking rate (MTR) 550. If pacing by the medical device is occurring at the lower rate limit (LRL) 560, anything sensed in the atrium between 0 and 250 milliseconds will be ignored. If pacing is based off of the maximum tracking rate (MTR) 550, anything sensed between 0 and 240 milliseconds will be ignored.

The left ventricular refractory period (LVRP) display 440 illustrates the timing that the ventricular sensing in the left ventricle is ignoring events following a left ventricular pace represented by Left Ventricle Pulse (LVP) indicator line 530. The LVRP display area 430 includes a parameter slide controllers 447 and an adjustment guide 443. The LVRP refractory period represented by the period from the edge of the Left Ventricular Pulse (LVP) indicator line 530 to the edge of the parameter slide controller 543, is not reflected is display 400 to scale. The actual LVRP refractory period is displayed in the parameter slide controller rate windows 445 and may be adjusted by horizontal movement of parameter slide controllers 443.

The left ventricular refractory period, which follows a left ventricular pulse 530, is 250 milliseconds. It begins at the left ventricular pulse 530 and ends at the edge of parameter slide controller 443. The actual refractory period timing parameter is illustrated in the parameter slide controller rate window 445. The left ventricular refractory period may be increased or decreased by sliding parameter slide controller 443 horizontally from 0 milliseconds beginning at the left ventricular pace 530 out to the maximum tracking rate (MTR) 550.

Display 400 also includes a diagram of a heart 500 that reflects the atrium 502, the right ventricle 504 and the left ventricle 506. The atrium 502, the right ventricle 504 and the left ventricle 506 are all shaded different colors. In the present embodiment the colors are blue for the atrium 502, magenta for the right ventricle 504 and orange for the left ventricle 506. It is to be understood that the colors reflected in the atrium 502, the right ventricle 504 and the left ventricle 506 may be any color so long as the colors are sufficient to identify a distinction between these chambers of the heart. The colored areas of the atrium 502, the right ventricle 504 and the left ventricle 506 correspond to the adjustment guides 407, 417, 427, 437, and 447 to reflect that for example in the AV delay, the adjustment guide 407 relates to delay in the atrium 502. The LV offset adjustment guide 417 relates to offset within the right ventricle 504. The refractory period adjustment guide 427 relates to the refractory period for the PVARP, which is associated with the atrium 502. The refractory period adjustment guide 437 relates to the refractory period for the RVRP, which is associated with the right ventricle 504, and the refractory period adjustment guide 447 relates to the refractory period for the LVRP, which is associated with the left ventricle 506.

Display 400 also includes a static ECG trace 501, illustrating how the respective components of an ECG trace, including P-wave 512 and the QRS of a R-wave 514. The atrial and ventricular waveforms P-wave 512 and the QRS of a R-wave 514 are adjusted based on timing parameters. For example, if the slide controller 403 is adjusted to decrease the maximum AV delay from 300 milliseconds to 250 milliseconds, the distance on the ECG trace from the atrial P-wave 512 to the ventricle R-wave 514 would also be decreased. The ECG trace also includes sensing window timing indicators 466 and 468 that illustrate sensing windows for the atrium 466 and sensing windows for the ventricle 468. Sensing windows 466 and 468 illustrate the beginning and ending of the atrial and ventricular sensing windows in relation to an ECG. Sensing windows 466 and 468 are also color coded to graphically indicate to the user via display 400 that the sensing window 466 relates to the atrium 502 and that the sensing window 468 relates to the right ventricle 504. In the embodiment illustrated in display 400 in FIGS. 5 and 6, sensing window 466 has is blue and sensing window 468 is magenta. It is to be understood that it is contemplated that the ECG trace 501 may not be static and may be an actual ECG trace of a patient illustrated dynamically in display 400.

Display 400 also utilizes the automatic responsive adjustment function that automatically illustrates to the user when there are conflicts within the timing cycle parameters. As illustrated in FIG. 6 of display 400, there are conflicts within timing cycle parameters for the AV delay minimum and the PVARP refractory period minimum, as illustrated in parameter slide controller rate windows 404 and 424. Within the AV delay display area 401, the adjustment guide 407a turns red and has crosshatches for the portion of the AV delay timing cycle that creates a parameter conflict, if the AV delay minimum parameters are within that range. In display 400, if the AV delay minimum, which is 80 milliseconds, is reduced to 50 milliseconds, the automatic response adjustment function would automatically remove the red crosshatches illustrated in 407a and 429a, thereby informing the system user automatically that the parameters selected are no longer in conflict.

In addition, the background of the timing parameters illustrated in parameter slide controller rate windows 404 and 424 have a red background to further indicate to the user which particular timing cycle parameters are in conflict. The system includes a myriad of rules that define circumstances during which modification or adjustments of timing cycle parameters may create conflict between parameters. Upon the adjustment of timing cycle parameters causing parameter conflicts, the red cross hatches would be illustrated on the adjustment guide of the appropriate timing cycle and the background of the parameter slide controller rate window would become red to illustrate that these particular parameters need to be adjusted. Upon adjustment of these values the red background within the parameter slide controller rate window would be changed back to green if it is a non-programmed value and to white if it the current value that is programmed within the medical device. As illustrated in FIG. 6, the display 400 includes a help button 492, which allows the system user to receive additional detail concerning the parameter conflicts created by the parameter adjustments made by the user.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

We claim:

1. A method comprising the acts of:
adjusting a first tachyarrhythmia rate threshold parameter of an implantable device by receiving user input for selecting and moving a first tachyarrhythmia rate threshold parameter controller;
processing said user input for adjusting the first tachyarrhythmia rate threshold parameter; and
generating an automatic adjustment to a related tachyarrhythmia rate threshold parameter related to said first tachyarrhythmia rate threshold parameter by causing automatic movement of a related tachyarrhythmia rate threshold parameter controller in response to said processing of said user input for adjusting the first tachyarrhythmia rate threshold parameter, wherein the first and the related tachyarrhythmia rate threshold parameters define tachyarrhythmia zones.

2. The method of claim 1, comprising generating an automatic adjustment to at least one of a maximum sensor rate, a maximum tracking rate, and a brady upper rate limit in response to receiving user input for selecting and moving a lowest tachyarrhythmia rate threshold.

3. The method of claim 2, in which the generating an automatic adjustment to at least one of a maximum sensor rate, a maximum tracking rate, and a brady upper rate limit in response to receiving user input for selecting and moving a lowest tachyarrhythmia rate threshold comprises maintaining at least one of the maximum sensor rate, the maximum tracking rate, and the brady upper rate limit to be at least a specified margin below the lowest tachyarrhythmia rate threshold.

4. The method of claim 1, comprising generating an automatic adjustment to at least one of a maximum sensor rate, a maximum tracking rate, and a brady upper rate limit in response to receiving user input for selecting and moving a lowest atrial tachyarrhythmia rate threshold.

5. The method of claim 4, in which the generating an automatic adjustment to at least one of a maximum sensor rate, a maximum tracking rate, and a brady upper rate limit in response to receiving user input for selecting and moving a lowest atrial tachyarrhythmia rate threshold comprises maintaining at least one of the maximum sensor rate, the maximum tracking rate, and the brady upper rate limit to be at least a specified margin below the lowest atrial tachyarrhythmia rate threshold.

6. The method of claim 4, in which the generating an automatic adjustment to at least one of a maximum sensor rate, a maximum tracking rate, and a brady upper rate limit in response to receiving user input for selecting and moving a lowest atrial fibrillation rate threshold comprises maintaining at least one of the maximum sensor rate, the maximum tracking rate, and the brady upper rate limit to be at least a specified margin below the lowest atrial fibrillation rate threshold.

7. The method of claim 1, in which moving the first tachyarrhythmia rate threshold controller comprises moving a first tachyarrhythmia rate threshold slide controller.

8. The method of claim 1, in which generating an automatic adjustment to a related tachyarrhythmia rate threshold parameter comprises adjusting a lowest tachyarrhythmia rate threshold (VT-1).

9. The method of claim 1, in which generating an automatic adjustment to a related rate threshold parameter comprises adjusting an intermediate tachyarrhythmia rate threshold (VT).

10. The method of claim 1, in which generating an automatic adjustment to a related rate threshold parameter comprises adjusting a highest tachyarrhythmia rate threshold (VF).

11. The method of claim 1, in which the generating an automatic adjustment to a related rate threshold parameter comprises maintaining at least a specified margin between sequentially adjacent tachyarrhythmia rate thresholds in response to receiving user input to adjust at least one of the tachyarrhythmia rate thresholds.

12. The method of claim 1, comprising generating an automatic adjustment to at least one of a maximum sensor rate, a maximum tracking rate, and a brady upper rate limit in response to receiving user input for selecting and moving an atrial fibrillation rate threshold.

13. An external programmer for programming an implantable device, the external programmer comprising:
a first tachyarrhythmia rate threshold parameter controller configured to adjust a first tachyarrhythmia rate threshold parameter of an implantable device by receiving user input for selecting and moving the first tachyarrhythmia rate threshold controller; and
a processor configured to process the user input and to automatically generate a responsive adjustment to a related tachyarrhythmia rate threshold parameter related to the first tachyarrhythmia rate threshold parameter by causing automatic movement of the related tachyarrhythmia rate threshold parameter.

14. The programmer of claim 13, in which the processor is configured to generate an automatic adjustment to at least one of a maximum sensor rate, a maximum tracking rate, and a brady upper rate limit in response to receiving user input for selecting and moving a lowest tachyarrhythmia rate threshold.

15. The programmer of claim 14, in which the processor is configured to generate an automatic adjustment to at least one of a maximum sensor rate, a maximum tracking rate, and a brady upper rate limit in response to receiving user input for selecting and moving a lowest tachyarrhythmia rate threshold so as to maintain at least one of the maximum sensor rate, the maximum tracking rate, and the brady upper rate limit to be at least a specified margin below the lowest tachyarrhythmia rate threshold.

16. The programmer of claim 13, in which the processor is configured to generate an automatic adjustment to at least one of a maximum sensor rate, a maximum tracking rate, and a brady upper rate limit in response to receiving user input for selecting and moving a lowest atrial tachyarrhythmia rate threshold.

17. The programmer of claim 16, in which the processor is configured to generate an automatic adjustment to at least one of a maximum sensor rate, a maximum tracking rate, and a brady upper rate limit in response to receiving user input for selecting and moving a lowest atrial tachyarrhythmia rate threshold so as to maintain at least one of the maximum sensor rate, the maximum tracking rate, and the brady upper rate limit to be at least a specified margin below the lowest atrial tachyarrhythmia rate threshold.

18. The programmer of claim 13, in which the processor is configured to generate an automatic adjustment to at least one of a maximum sensor rate, a maximum tracking rate, and a brady upper rate limit in response to receiving user input for selecting and moving an atrial tachyarrhythmia rate threshold.

19. The programmer of claim 18, in which the processor is configured to generate an automatic adjustment to at least one of a maximum sensor rate, a maximum tracking rate, and a brady upper rate limit in response to receiving user input for selecting and moving an atrial tachyarrhythmia rate threshold so as to maintain at least one of the maximum sensor rate, the maximum tracking rate, and the brady upper rate limit to be at least a specified margin below the atrial tachyarrhythmia rate threshold.

20. The programmer of claim 13, in which the first tachyarrhythmia rate threshold controller includes a slide controller.

21. The programmer of claim 13, in which the processor is configured to generate an automatic adjustment to a related tachyarrhythmia rate threshold parameter by adjusting a lowest tachyarrhythmia rate threshold (VT-1).

22. The programmer of claim 13, in which the processor is configured to generate an automatic adjustment to a related tachyarrhythmia rate threshold parameter by adjusting an intermediate tachyarrhythmia rate threshold (VT).

23. The programmer of claim 13, in which the processor is configured to generate an automatic adjustment to a related tachyarrhythmia rate threshold parameter by adjusting a highest tachyarrhythmia rate threshold (VF).

24. The programmer of claim 13, in which the processor is configured to generate an automatic adjustment to a related rate threshold parameter so as to maintain at least a specified margin between sequentially adjacent tachyarrhythmia rate thresholds in response to receiving user input to adjust at least one of the tachyarrhythmia rate thresholds.

25. An apparatus comprising:
means for adjusting a first tachyarrhythmia rate threshold parameter of an implantable device by receiving user input for selecting and moving a first tachyarrhythmia rate threshold parameter controller;

means for processing said user input for adjusting the first tachyarrhythmia rate threshold parameter; and means for generating an automatic adjustment to a related tachyarrhythmia rate threshold parameter related to said first tachyarrhythmia rate threshold parameter by causing automatic movement of the related tachyarrhythmia rate threshold parameter controller in response to said processing of said user input for adjusting the first tachyarrhythmia rate threshold parameter.

* * * * *

UNITED STATES PATENT AND TRADEMARK OFFICE
CERTIFICATE OF CORRECTION

| | |
|---|---|
| PATENT NO. | : 7,272,444 B2 |
| APPLICATION NO. | : 10/841966 |
| DATED | : September 18, 2007 |
| INVENTOR(S) | : Peterson et al. |

It is certified that error appears in the above-identified patent and that said Letters Patent is hereby corrected as shown below:

On the Title Page, under "Abstract", Item (57), line 5, before "slide" insert -- user --

On the Title Page, under "Abstract", Item (57), line 8, after "parameters" delete ".".

In column 15, line 65, delete "though" and insert -- through --, therefor.

In column 16, line 23, delete "RVIRP" and insert -- RVRP --, therefor.

In column 17, line 32, after "501" delete ",".

Signed and Sealed this

Eighteenth Day of December, 2007

JON W. DUDAS
*Director of the United States Patent and Trademark Office*